(12) United States Patent
Jung et al.

(10) Patent No.: US 8,901,289 B2
(45) Date of Patent: Dec. 2, 2014

(54) PREPARATION OF NUCLEOTIDE OLIGOMER

(75) Inventors: Kyeong-Eun Jung, Anyang-si (KR); Alexei Kayushin, Moscow (RU); Moon Hee Kim, Seoul (KR); Kyung-Il Kim, Seongnam-si (KR); Sungwon Kim, Daejeon (KR); Yumi Ji, Gunpo-si (KR)

(73) Assignee: St. Pharm Co., Ltd., Gyeonggi-do (KR)

( * ) Notice: Subject to any disclaimer, the term of this patent is extended or adjusted under 35 U.S.C. 154(b) by 565 days.

(21) Appl. No.: 12/775,843

(22) Filed: May 7, 2010

(65) Prior Publication Data

US 2010/0273999 A1     Oct. 28, 2010

Related U.S. Application Data

(63) Continuation-in-part of application No. PCT/KR2008/006674, filed on Nov. 12, 2008.

(30) Foreign Application Priority Data

Nov. 13, 2007 (KR) ........................ 10-2007-0115302

(51) Int. Cl.
| | | |
|---|---|---|
| C07H 21/02 | (2006.01) | |
| C07H 19/167 | (2006.01) | |
| C07H 19/067 | (2006.01) | |
| C07H 19/10 | (2006.01) | |
| C07H 19/20 | (2006.01) | |

(52) U.S. Cl.
CPC .............. *C07H 21/02* (2013.01); *C07H 19/167* (2013.01); *C07H 19/067* (2013.01); *C07H 19/10* (2013.01); *C07H 19/20* (2013.01)
USPC ..................................... 536/25.34; 536/25.33

(58) Field of Classification Search
None
See application file for complete search history.

(56) References Cited

U.S. PATENT DOCUMENTS

| | | | | | |
|---|---|---|---|---|---|
| 4,310,662 | A | * | 1/1982 | Crea ........................... | 536/25.31 |
| 6,060,456 | A | * | 5/2000 | Arnold et al. ................ | 514/44 A |
| 6,436,675 | B1 | * | 8/2002 | Welch et al. ................. | 435/91.1 |

FOREIGN PATENT DOCUMENTS

| | | | | |
|---|---|---|---|---|
| WO | WO02/22634 | * | 3/2002 | ............. C07H 21/00 |
| WO | WO 0220543 A2 | | 3/2002 | |
| WO | WO 0220543 A3 | | 3/2002 | |

OTHER PUBLICATIONS

Lyttle et al., "Mutagenesis using Trinucleotide beta-cyanoethylphosphoramidites" BioTechniques (1995) vol. 19, pp. 274-281.*
Zhong et al., "Synthesis of the Ribosomal P-Site Substrate CCA-pcb" Organic Letters (2006) vol. 8 No. 1 pp. 55-58.*
Grams et al., "Synthesis of a Diribonucleoside Monophosphate by the beta-Cyanoethyl Phosphotriester Method" The Journal of Organic Chemistry (1970) vol. 35 No. 3, pp. 868-870.*
Abstract of Korean Patent No. KR1020030081303 dated Oct. 17, 2003, 1 page.
Zhong et al., *Synthesis of Isotopic ally Labeled P-Site Substrates for the Ribosomal Peptidyl Transferase Reaction*, J. Org. Chem., 2008, vol. 73, No. 2, pp. 603-611.
Ogilvie et al, *Synthesis of Oligoribonucleotides*, Journal of the American Chemical Society, vol. 99, No. 23, Nov. 9, 1977, pp. 7741-7743.
Ogilvie et al., *The synthesis of oligorbonucleotides. II.[1] The use of silyl protecting groups in nucleotide and nucleoside chemistry. VII[2]*, Can. J. Chem., vol. 56, 1978, pp. 2768-2780.
Search Report for PCT/KR2008/006674, dated Apr. 14, 2009, 4 pages.
Abstract of Article—Kim et al., "Synthesis of RNA Dimer and Trimer Blocks and Their Uses," *Nucleic Acids Symposium*, vol. 52, No. 1, Sep. 8, 2008, 1 page.
Article—Eleuteri et al., "Oligodeoxyribonucleotide Phosphorothioates: Substantial Reduction of (N-1)-Mer Content Through the Use of Trimeric Phosphoramidite Synthons," *Nucleosides & Nucleotides*, vol. 18, No. 3, Jan. 1, 1999, pp. 475-483.
Article—Krotz et al., "Phosphorothioate Oligonucleotides: Largely Reduced (N-1)-Mer and Phosphodiester Content Through the Use of Dimeric Phosphoramidite Snythons," *Bioorganic & Medicinal Chemistry Letters*, vol. 7, No. 1, Jan. 7, 1997, pp. 73-78.
Article—Seki et al., Formation of Interribonucleoside Phosphate Bond by the Use of Reagent Formed by the Reaction of 2-Chlorophenyl Phosphorodichloridate with 5-Nitrobenzotriazole and Preparation of Anticodon Triplet of Yeast tRNA$^{Lys\#}$, *Chemistry Letters*, No. 5, Jan. 1, 1987, pp. 775-778.
Article—Tanaka et al., "Synthesis of Oligoribonucleotides via the Phosphite-Triester Approach on a Polymer Support," *Chemical & Pharmaceutical Bulletin*, vol. 34, No. 10, Jan. 1, 1986, pp. 4126-4132.
Article—Takaku et al., "A Convenient Method for Insertion of the 5'-Terminal Phosphate Group in the Triester Approach to Oligoribonucleotide Synthesis," *The Journal of Organic Chemistry.*, vol. 45, No. 16, Aug. 1, 1980, pp. 3347-3350.
Article—Zehl et al., "Efficient and flexible access to fully protected trinucleotides suitable for DNA synthesis by automated phosphoramidite chemistry," *Chemical Communications*, vol. 23, Jan. 1, 1996, pp. 2677-2678.
Extended European Search Report for 08851003.7-2101 / 2217612 PCT/KR2008/006674 dated Feb. 1, 2013, 10 pages.

* cited by examiner

*Primary Examiner* — Eric Olson
(74) *Attorney, Agent, or Firm* — Dority & Manning, P.A.

(57) ABSTRACT

The present invention provides a method for preparing nucleotide oligomers, including (a) coupling a nucleotide dimer or nucleotide trimer to a nucleoside attached to solid supports or to universal solid supports as a starting material; (b) sequentially coupling nucleotide monomers to the resulting structures of Step (a) to prepare a nucleotide oligomer; and (c) removing the nucleotide oligomers from the solid supports. The method of the present invention provides nucleotide oligomers having 15-20% higher purity than the conventional art. The present invention enables the efficient and inexpensive synthesis of nucleotide oligomers with high purity within a shorter period of time.

11 Claims, No Drawings

PREPARATION OF NUCLEOTIDE OLIGOMER

CROSS-REFERENCE TO RELATED APPLICATION

This application is a Continuation-in-part of International Application No. PCT/KR2008/006674, filed Nov. 12, 2008, which claims priority from Korean Patent Application No. 10-2007-0115302, filed on Nov. 13, 2007. The contents of International Application and Korean Patent Application are herein incorporated by reference in their entireties.

TECHNICAL FIELD

The present invention relates to a method for preparing nucleotide oligomers. More specifically, the present invention relates to solid-phase synthesis of oligoribonucleotides.

BACKGROUND ART

There are known a variety of techniques for the preparation of nucleotide oligomers.

For example, methods of preparing the nucleotide oligomers can be found in the following references: Khorana et al., J. Molec. Biol. 72:209 (1972); Reese, Tetrahedron Lett. 34:3143 (1978); Beaucage and Caruthers, Tetrahedron Lett. 22:1859 (1981); U.S. Pat. No. 5,149,798; Agrawal and Goodchild, Tetrahedron Lett. 28:3539 (1987); Connolly et al. Biochemistry 23, 3443 (1984); Jager et al., Biochemistry 27:7237 (1988); Agrawal et al. Proc. Natl. Acad. Sci. USA 85:7079 (1988), e.g., Methods in Molecular Biology, Vol. 20, Protocols for Oligonucleotides and Analogs, p. 63-80 (S. Agrawal, Ed., Humana Press 1993); Methods in Molecular Biology, Vol. 26: Protocols for Oligonucleotide Conjugates (Agrawal, Ed., Humana Press, Totowa, N.J. 1994); Oligonucleotides and Analogues: A Practical Approach pp. 155-183 (Eckstein, Ed., IRL Press, Oxford 1991); Antisense Res. and Applns. pp. 375 (Crooke and Lebleu, Eds., CRC Press, Boca Raton, Fla. 1993); and Gene Regulation: Biology of Antisense RNA and DNA (Erickson and Izant, eds., Raven Press, New York, 1992).

Anti-sense RNA hybridizes to nucleic acid molecules to result in the inhibition of gene expression. Many researchers have reported the inhibition of expression of specific genes or therapeutic feasibility of particular diseases via the use of the antisense RNA (Barker et al. Proc. Natl. Acad. Sci. USA 93:514 (1996); Agrawal et al., Proc. Natl. Acad. Sci. USA 85:7079 (1988); Letter et al., Proc. Natl. Acad. Sci. USA 87:3420-3434 (1990); and Offensperger et al. EMBO J. 12:1257 (1993)).

Meanwhile, RNA-mediated interference (RNAi) is a phenomenon in which a 21-25-nucleotide small RNA fragment selectively binds to and degrades mRNA having a complementary sequence, thus resulting in the suppression of protein expression (Shen C, et al., FEBS Lett. 539 (1-3):111-4 (2003)). The RNAi phenomenon was first discovered in 1995 as a part of the gene-regulation mechanism in *Caenorphabditis elegans* and plants. In 1998, Dr. Andrew Fire of the Carnegie Institution of Washington and Dr. Craig Mello of the University of Massachusetts Medical School, and their team experimentally found that the expression of a specific gene can be significantly inhibited when double-stranded RNA (dsRNA) corresponding to a base sequence of the specific gene is in-vivo injected into *C. elegans* (Fire A, et al., Nature. 391 (6669):806-11 (1998)). The long-chain dsRNA injected into *C. elegans* is cleaved into a short double-stranded RNA fragment called small interfering RNA (siRNA) about 21-25 by long, by the enzymatic action of Dicer belonging to a member of the RNase III family of nucleases which specifically cleave double-stranded RNAs. The resulting short dsRNA is then incorporated into the RNA-induced silencing complex (RISC) where the siRNA duplex is unwound into two strands. Thereafter, the siRNA separated into single-strands binds to a specific gene mRNA with a complementary sequence and makes it untranslatable, thus inhibiting the expression of the corresponding gene. Further, Elbashir and his colleagues have reported that the expression of a specific gene can be selectively inhibited by injection of short dsRNA (siRNA) consisting of 21 bases into cultured mammalian cells, this finding leading to significant increases in practical applicability of RNAi in mammalian cells (Elbashir, S. M. et al., Nature 411 (6836):494-8 (2001)).

At present, siRNA-mediated gene expression inhibition techniques are widely used in functional understanding of various genes and a great deal of research has been actively focused on exploitation of such siRNAs for development of therapeutic agents for the treatment of intractable diseases such as cancers, infectious diseases, etc. (Mouldy Sioud. *Therapeutic siRNAs. Trends in pharmacological Sciences* 2004; 22-28).

As discussed above, many attempts have been made to develop therapeutic agents or diagnostic agents using antisense RNAs and siRNAs. To this end, there is an urgent need for an efficient mass production scheme of oligoribonucleotides.

Synthesis of nucleotide oligomers is usually carried out by sequential coupling of monomer units on solid resins, using an automatic DNA/RNA (or oligonucleotide) synthesizer. DNA oligomers can be synthesized with a good yield. On the other hand, synthesis of RNA oligomers, e.g. ribonucleotide oligomers entails various disadvantages due to steric hindrance of a protecting group for a 2'-OH group, such as long synthesis period and low coupling efficiency resulting in low production yield, thus making it difficult to obtain high-purity RNA oligos.

Throughout the specification, numerous scientific articles and patent publications are cited and citations thereof are identified. Disclosures of the cited articles and patent references are incorporated by reference herein in their entirety, such that a current status of a technical field to which the present invention pertains and the disclosure of the present invention will be more clearly described.

DISCLOSURE OF THE INVENTION

Technical Problem

As a result of a variety of extensive and intensive studies and experiments to solve the problems as described above and to find a method which is capable of achieving a convenient and high-purity production of oligomer species such as nucleotide oligomers, particularly ribonucleotide oligomers or small interfering RNAs (siRNAs), the inventors of the present invention discovered that it is possible to achieve the production of the nucleotide oligomers having significantly improved purity, through the use of a nucleotide dimer or nucleotide trimer as the first nucleotide synthon which will bind to solid supports. The present invention has been completed based on these findings.

Therefore, the object of the present invention is to provide a method for preparing nucleotide oligomers.

Technical Solution

Impurities produced during the synthesis of nucleotide oligomers are composed mainly of short sequences having a less degree of coupling than full-length sequences (Nmers), and they are usually expressed as (N−1)mers, (N−2)mers, (N−x)mers, or the like. Impurity oligomers shorter than the full-length Nmers are mostly produced due to the incomplete capping in a capping step of the product following the coupling reaction, upon coupling of nucleotide units to solid supports.

Further, impurity species which are most difficult to separate during the purification of desired nucleotide oligomers are (N−1)mers that are eluted at a position close to that of the desired oligomers on chromatograms.

However, according to the present invention using a dimer or trimer, not a monomer, in the first coupling reaction, the occurrences of (N−1)mers that are difficult to remove during the purification process are prevented and pure nucleotide oligomers are easily obtained with the formation of readily purifiable (N−2)mers or (N−3)mers. Particularly when it is desired to use the nucleotide oligomers as therapeutics, they are purified by chromatography techniques. In this respect, the Nmers and (N−1)mers are eluted at a very close time point, so it is difficult to satisfactorily accomplish the chromatographic separation of the (N−1)mers. However, when a nucleotide dimer or trimer is used as the first nucleotide block being coupled to solid supports, as disclosed in the present invention, the formation of (N−1)mer impurities is significantly decreased, thus leading to pronounced improvements of purification yields and consequently significant reductions of production costs.

As will be demonstrated in Examples which will follow hereinafter, the present invention enables reductions of the (N−1)mers that are mostly produced largely in the first coupling reaction, as well as overall decreases of (N−x)mer impurities. This is believed to be due to that when the coupling of a longer dimer or trimer instead of a monomer is made in the first coupling reaction on solid-supports, the next binding of a monomer to the coupled dimer or trimer is much more spatially advantageous than the binding of a next monomer to a non-capped site, which consequently lessens the formation of oligomers having a sequence length shorter than a desired oligomer.

Further, the present invention provides the following differences and excellent effects, as compared to the conventional art (PCT/GB2001/03973).

① Conventional art employs only dimers for the synthesis of nucleotide oligomers and therefore prepares the nucleotide oligomers of a dimer repeating sequence, whereas the present invention relates to the preparation of the nucleotide oligomers, involving the use of a dimer or trimer unit only in the first coupling reaction on solid supports. That is, the conventional art requires various kinds of dimers of up to 10 kinds, when it is desired to prepare siRNA oligomers using dimer units. In other words, it is necessary to synthesize 10 kinds of dimers for this purpose, thus requiring long-term periods of synthesis and high production costs. In contrast, the present invention employs just one dimer or trimer species only in the first coupling step and then common inexpensive monomer units in the subsequent steps, which enables the low-cost, high-purity production of the nucleotide oligomers.

② Further, the present invention achieves a shorter synthesis time than the conventional art. Typically, a coupling reaction of RNA nucleotide oligomer synthesis takes a 10 times longer period of time than DNA nucleotide oligomer synthesis. In this connection, although the conventional art deals with a synthesis example of DNA nucleotide oligomers, it suggested that a coupling reaction of DNA dimers takes a period of 20 to 60 min. On the other hand, according to the present invention, the coupling of the first dimer for the synthesis of RNA nucleotide oligomers takes 10 to 20 min and the subsequent monomer coupling takes 10 min, so the total synthesis time is much shorter than the conventional art. As a consequence, the present invention shortens production periods of products to thereby significantly reduce production costs, when the nucleotide oligomers are formulated into therapeutics.

The present invention provides a method for preparing nucleotide oligomers, comprising the steps of:

(a) coupling a nucleotide dimer or nucleotide trimer to a nucleoside attached to solid supports or to universal solid supports as a starting material;

(b) sequentially coupling nucleotide monomers to the resulting structures of Step (a) to prepare nucleotide oligomers; and (c) removing the nucleotide oligomers from the solid supports.

In one embodiment of the present invention, the method for preparing nucleotide oligomers preferably includes the steps of:

(a) coupling a nucleotide dimer to a nucleoside attached to solid supports or to universal solid supports as a starting material;

(b) sequentially coupling nucleotide monomers to the resulting structures of Step (a) to prepare nucleotide oligomers; and (c) removing the nucleotide oligomers from the solid supports.

In another embodiment of the present invention, the method for preparing nucleotide oligomers preferably includes the steps of:

(a) coupling a nucleotide trimer to a nucleoside attached to solid supports or to universal solid supports as a starting material;

(b) sequentially coupling nucleotide monomers to the resulting structures of Step (a) to prepare nucleotide oligomers; and (c) removing the nucleotide oligomers from the solid supports.

As used herein, unless otherwise indicated, the term "nucleotide" is intended to encompass ribonucleotides, deoxyribonucleotides and derivatives thereof.

As used herein, the term "ribonucleotide" refers to a nucleotide that has no 2'-H of a carbon atom at position 2 of sugar, and is intended to encompass naturally-occurring ribonucleotides as well as analogues thereof. In the context of the present invention, for example, the term "ribonucleotide" also embraces derivatives of ribonucleotides where alkyl (for example, methyl or ethyl) is bonded to —OH on the C2 carbon of sugar or a halogen atom (for example, fluoro) or amino group instead of —OH is bonded to the C2 carbon of sugar.

The term "deoxyribonucleotide" refers to a nucleotide that contains 2'-H of sugar, and is intended to encompass naturally-occurring deoxyribonucleotides as well as analogues thereof.

Examples of the nucleotide in the context of the present invention may include backbone-modified nucleotides such as phosphorothioate DNA or RNA, phosphorodithioate DNA or RNA, and phosphoramidate DNA or RNA; sugar-modified nucleotides such as 2'-O-methyl RNA, 2'-O-ethyl RNA, 2'-O-methoxyethyl RNA, 2'-fluoro RNA, T-halogen RNA, 2'-amino RNA, 2'-O-alkyl RNA, 2'-O-alkoxy RNA, 2'-O-alkyl DNA, 2'-O-allyl DNA, 2'-O-alkynyl DNA, hexose DNA, pyranosyl RNA, anhydrohexitol DNA, and locked nucleic acid (LNA); and base-modified nucleotides comprising a base such as C-5 substituted pyrimidines (substituents include fluoro-, bromo-, chloro-, iodo-, methyl-, ethyl-, vinyl-, formyl-, ethynyl-, propynyl-, alkynyl-, thiazolyl-, imidazolyl-, and pyridyl-), 7-deazapurines with C-7 substituents (substituents include fluoro-, bromo-, chloro-, iodo-, methyl-, ethyl-, vinyl-, formyl-, alkynyl-, alkenyl-, thiazolyl-, imidazolyl-, and pyridyl-), inosine and diaminopurine.

The nucleotide of the present invention is preferably a ribonucleotide, more preferably a ribonucleoside phosphoramidite.

Therefore, the nucleotide oligomer of the present invention may include various kinds of nucleotide oligomers, e.g. deoxyribonucleotide oligomers, ribonucleotide oligomers and their derivatives. More specifically, the present invention covers naturally-occurring nucleotide oligomers as well as modified nucleotide oligomers. For example, there may be mentioned backbone-modified nucleotide oligomers such as phosphorothioate DNA or RNA, phosphorodithioate DNA or RNA, and phosphoramidate DNA or RNA; sugar-modified nucleotide oligomers such as 2'-O-methyl RNA, 2'-O-ethyl RNA, 2'-O-methoxyethyl RNA, 2'-fluoro RNA, 2'-halogen RNA, 2'-amino RNA, 2'-O-alkyl RNA, 2'-O-alkoxy RNA, 2'-O-alkyl DNA, 2'-O-allyl DNA, 2'-O-alkynyl DNA, hexose DNA, pyranosyl RNA, anhydrohexitol DNA, and locked nucleic acid (LNA); and base-modified nucleotide oligomers such as C-5 substituted pyrimidines (substituents include fluoro-, bromo-, chloro-, iodo-, methyl-, ethyl-, vinyl-, formyl-, ethynyl-, propynyl-, alkynyl-, thiazolyl-, imidazolyl-, and pyridyl-), 7-deazapurine with C-7 substituents (substituents include fluoro-, bromo-, chloro-, iodo-, methyl-, ethyl-, vinyl-, formyl-, alkynyl-, alkenyl-, thiazolyl-, imidazolyl-, and pyridyl-), inosine and diamino purine.

The nucleotide oligomer of the present invention is preferably a ribonucleotide oligomer.

Preferably, the nucleotide oligomer is one containing at least one ribonucleotide selected from 2'-O-halogen ribonucleotide, 2'-amino ribonucleotide, 2'-O-alkyl ribonucleotide and 2'-O-alkoxy ribonucleotide. For example, the ribonucleotide may include 2'-O-flora ribonucleotide, 2'-O-methyl ribonucleotide or 2'-O-methoxy ribonucleotide. These may be used alone or in a mixture thereof.

The present invention employs the nucleotide dimer or nucleotide trimer as the first coupling reactant that will be attached to solid supports. Depending on the kinds of nucleotides positioned at the 3'-terminus corresponding to the third carbon of sugar, e.g. the kinds of nucleotides bonded to the solid supports, the method of the present invention can be classified into 3 types as follows:

① The first one is a case where the nucleoside is positioned at the 3'-terminus. That is, the nucleotide dimer or nucleotide trimer as the first coupling reactant is coupled to solid supports on which a nucleoside monomer as a starting material of a synthesis process was preloaded, followed by sequential coupling of nucleotide monomers to the resulting structure to thereby prepare a nucleotide oligomer having a desired sequence.

② The second one is a case where the nucleotide dimer is positioned at the 3'-terminus. This case employs universal solid supports as a starting material. The universal solid supports as a starting material are employed in the first step of the synthesis process, and the nucleotide dimer is employed as the first coupling reactant. Thereafter, nucleotide monomers are sequentially coupled to the resulting structure to thereby prepare a nucleotide oligomer having a desired sequence.

③ The third one is a case where the nucleotide trimer is positioned at the 3'-terminus. This case also employs the universal solid supports as a starting material. The universal solid supports as a starting material are employed in the first step of the synthesis process, and the nucleotide trimer is employed as the first coupling reactant. Thereafter, nucleotide monomers are sequentially coupled to the resulting structure to thereby prepare a nucleotide oligomer having a desired sequence.

The most preferred one out of the above-mentioned three methods is a method where the solid supports to which one nucleoside was previously attached are employed as a starting material and the nucleotide dimer or timer as the first coupling reactant is then coupled to the preloaded nucleoside.

As used herein, the term "universal solid supports" refers to solid supports that are free of a nucleoside or nucleotide oligomer covalently bonded thereto. Unlike the preloaded supports, the use of the universal solid supports enables the synthesis of any nucleotide oligomer regardless of the kinds of terminal sequences of the nucleotide oligomers. When the universal supports are employed, a terminal sequence of the final synthetic nucleotide oligomer is determined by a nucleotide synthon applied to the first coupling reaction of the nucleotide oligomer synthesis.

The present invention is practiced according to solid phase synthesis.

When the process of the present invention is carried out according to solid phase synthesis, a preferred embodiment of the present invention includes the following steps of:

(a) coupling a nucleotide dimer [$(NMP)_2$] or nucleotide trimer [$(NMP)_3$] to [$(NS)_1$] of a solid support-nucleoside [SS—$(NS)_1$] to prepare SS—$(NS)_{1\text{-}}(NMP)_2$ or SS—$(NS)_{1\text{-}}(NMP)_3$;

(b) sequentially coupling nucleotide monomers to the resulting structure of Step (a) to prepare an SS—$(NS)_{1\text{-}}(NMP)_{2\text{-}}(NMP)_{n-3}$ or SS—$(NS)_{1\text{-}}(NMP)_{3\text{-}}(NMP)_{n-4}$; and (c) removing the solid supports (SS) from the SS—$(NS)_{1\text{-}}(NMP)_{2\text{-}}(NMP)_{n-3}$ or SS—$(NS)_{1\text{-}}(NMP)_{3\text{-}}(NMP)_{n-4}$ structure to obtain an $(NMP)_n$.

When the nucleotide dimer [$(NMP)_2$] or nucleotide trimer [$(NMP)_3$] is coupled in the first step to the solid supports to which a nucleoside monomer was previously attached, and nucleotide monomers are then sequentially coupled thereto, a nucleotide oligomer molecule can be prepared with significantly improved purity.

The solid support-nucleoside [SS—$(NS)_1$] is a structure where one ribonucleoside or deoxyribonucleoside molecule was attached to the solid supports. The solid supports may be any one that is used in the solid phase synthesis of nucleotide molecules. Alternatively, there may also be employed universal solid supports to which ribonucleoside or deoxyribonucleoside was not previously attached. Preferably, such solid supports should have the following properties: (i) substantially no solubility in the reagents used for the nucleotide oligomer synthesis, (ii) chemical stability against reagents used for nucleotide oligomer synthesis, (iii) feasibility of chemical modifications, (iv) loadability of desired nucleotide oligomers, (v) reasonable compression strength to withstand increasing pressure during the synthesis process, and (vi) desired particle size and distribution.

A material that can be used as the solid supports in the present invention may be preferably an inorganic polymer and include, for example, silica, porous glass, aluminum silicate, polystyrene, polyvinyl alcohol, polyvinyl acetate, borosilicate, metal oxide (such as alumina and nickel oxide) and clay. Most preferably, the solid supports for use in the present invention are controlled pore glass (CPG) and polystyrene.

The present invention employs an [SS—$(NS)_1$] where a nucleoside was previously attached to a surface of the solid supports, preferably an [SS-$(rNS)_1$] where a ribonucleoside was attached to a surface of the solid supports. The nucleoside is conventionally attached to the solid supports through a 3'-OH group of sugar.

The coupling of the nucleotide dimer or nucleotide trimer to the [SS—(NS)$_1$] may be carried out by various methods known in the art. For example, details of the coupling method can be found in the following literature: U.S. Pat. Nos. 4,458,066 and 4,415,732; Caruthers et al., *Genetic Engineering*, 4:1-17 (1982); and Users Manual Model 392 and 394 Polynucleotide Synthesizers, pages 6-1 through 6-22, Applied Biosystems, Part No. 901237 (1991).

Preferably, the coupling process is carried out according to a phosphoramidite method. For example, it may be performed as follows. A phosphoramidite derivative of the nucleotide dimer [(NMP)$_2$] or nucleotide trimer [(NMP)$_3$] is added to the [SS—(NS)$_1$] while simultaneously an activator, for example a weak acid (such as tetrazole, 5-ethylthiotetrazole, benzylthiotetrazole, etc.) is added. Most preferably, the usable activator is 5-ethylthiotetrazole. Addition of the weak acid leads to the formation of a reaction intermediate through protonation of phosphoramidite nitrogen. This is followed by the capping of the resulting product. The capping is preferably carried out with an acetic anhydride and 1-methylimidazole. Then, the capped product is oxidized using an oxidant such as iodine, so that an internucleotide linkage is converted into a more stable phosphodiester from labile phosphite. The order of capping and oxidation steps may be reversed. Following the oxidation step, a hydroxyl-protecting group is removed using a protic acid, for example, trichloroacetic acid or dichloroacetic acid.

The nucleotide dimer [(NMP)$_2$] or nucleotide trimer [(NMP)$_3$] of the present invention may have various kinds of linkages, preferably phosphodiester, phosphoramidate, alkylphosphoramidate, alkylphosphonate, phosphorothioate, alkylphosphotriester, or alkylphosphonothioate linkages, most preferably phosphodiester or phosphoramidate linkages.

Preferably, the nucleotide dimer [(NMP)$_2$] and the nucleotide trimer [(NMP)$_3$] of the present invention are the nucleotide dimer phosphoramidite and the nucleotide trimer phosphoramidite, respectively.

Therefore, the nucleotide oligomer of the present invention has a phosphodiester, phosphoramidate, alkylphosphoramidate, alkylphosphonate, phosphorothioate, alkylphosphotriester, or alkylphosphonothioate linkage, most preferably a phosphodiester or phosphoramidate linkage.

According to the present invention, the SS—(NS)$_1$-(NMP)$_2$-(NMP)$_{n-3}$ or SS—(NS)$_1$-(NMP)$_3$-(NMP)$_{n-4}$ having a desired sequence is finally prepared by sequential coupling of the ribonucleotide monomers to the nucleotide dimer [(NMP)$_2$] or nucleotide trimer [(NMP)$_3$] attached to the solid support-nucleoside [SS—(NS)$_1$].

When the nucleotide monomers are sequentially coupled, 5-ethylthiotetrazole is used as an activator.

Finally, the desired product (NMP)$_n$ is obtained by removal of the solid supports (SS) from the SS—(NS)$_1$-(NMP)$_2$-(NMP)$_{n-3}$ or SS—(NS)$_1$-(NMP)$_3$-(NMP)$_{n-4}$. When there is used the universal solid supports with no attachment of ribonucleoside or nucleoside, the (NMP)$_n$ is obtained by removal of the solid supports (SS) from the SS—(NMP)$_2$-(NMP)$_{n-2}$ or SS—(NMP)$_3$-(NMP)$_{n-3}$.

Removal of the solid supports may be carried out by any conventional method known in the art. For example, the solid supports may be eliminated using ammonium hydroxide.

According to the preferred embodiment of the present invention, the method of the present invention may further include a step of removing the protecting groups attached to the nucleotide oligomer [(NMP)$_n$], before or after Step (c). Removal of the protecting groups may be carried out by any conventional method known in the art. For example, a phosphate protecting group may be removed with the treatment of thiophenol or ammonium hydroxide solution, whereas benzoyl and isobutyryl groups attached to the base may be removed by heating the nucleotide oligomer in an ammonium hydroxide solution.

There is no particular limit to a length of the nucleotide oligomer [(NMP)$_n$] prepared by the method of the present invention. Typically, the nucleotide oligomer is 10 to 50 nucleotides in length.

According to the method of the present invention, it is possible to efficiently synthesize a high-purity nucleotide oligomer, particularly an oligoribonucleotide within a shorter period of time. The method of the present invention provides a nucleotide oligomer having 15-20% higher purity than the conventional art.

Further, the present invention provides a ribonucleotide dimer represented by Formula 5 below:

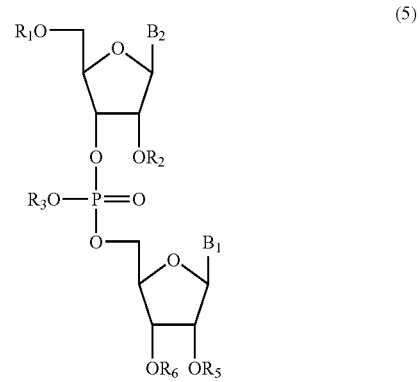

(5)

wherein R$_1$, R$_2$, R$_3$ and R$_5$ are each independently hydrogen (—H) or protecting groups, B$_1$ and B$_2$ are each independently nucleosidic bases, and R$_6$ is hydrogen or

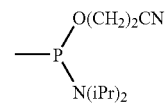

wherein iPr is isopropyl.

Preferred is the ribonucleotide dimer of Formula 5 wherein R$_1$ is hydrogen (—H) or dimethoxytrityl; R$_2$ and R$_5$ are each t-butyl-dimethylsilyl; and R$_3$ is halogen-substituted phenyl.

Further, the present invention provides a method for preparing a nucleotide dimer, comprising coupling of a compound of Formula 1 and a compound of Formula 2:

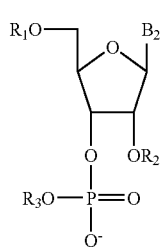

(1)

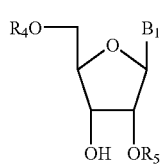

(2)

In Formulae 1 and 2, $R_1$, $R_2$, $R_3$, $R_4$ and $R_5$ are each independently hydrogen (—H) or protecting groups, and $B_1$ and $B_2$ are each independently nucleosidic bases.

Examples of the protecting groups $R_1$ and $R_4$ in Formulae 1 and 2 may independently include, but are not limited to, hydrogen (—H), dimethoxytrityl, monomethoxytrityl, trityl, and 9-phenyl xanthen-9-yl (pixyl). Preferred examples of suitable groups for $R_2$ and $R_5$ may independently include, but are not limited to, t-butyl-dimethylsilyl, tri-isopropyl silyloxymethyl (TOM), 1-(2-chloro ethoxy)ethyl (CEE), 2-cyanoethoxymethyl (CEM), bis(2-acetoxy)methyl (ACE), 1-(2-fluorophenyl)-4-methoxypiperidin-4-yl (Fpmp), 1-(4-chloro phenyl)-4-ethoxypiperidin-4-yl (Cpep), 1-[2-chloro-4-methyl)phenyl]-4-methoxy piperidin-4-yl (Ctmp), 4-nitrophenylethylsulfonyl (NPES), 4-chloro phenylethylsulfonyl (CPES), 1-(2-cyanoethoxy)ethyl (CNEE), trimethyl silylethoxymethyl (SEM), methoxyethoxymethyl (MEM), levulinyl, 4-nitropheylethyl (NPE), and 4-nitrophenylethyloxycarbonyl (NPEOC).

$R_3$ is preferably halogen-substituted phenyl or carbobenzoxyl, without being limited thereto. Each of $B_1$ and $B_2$ is independently adenine, cytosine, guanine, uracil or a derivative thereof.

More preferably, in Formulae 1 and 2, $R_1$ and $R_4$ are independently hydrogen (—H) or dimethoxytrityl, $R_2$ and $R_5$ are t-butyl-dimethylsilyl, and $R_3$ is halogen-substituted phenyl (most preferably 2-chlorophenyl).

Each of $B_1$ and $B_2$ is a base to which a protecting group is attached or not. Examples of the base that can be positioned on $B_1$ and $B_2$ may include common bases such as adenine, cytosine, guanine and uracil, as well as their derivatives. Preferably, derivatives of the bases include xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil and cytosine, 5-uracil (pseudo uracil), 4-thiouracil, 8-halo, oxa, amino, thiol, thioalkyl and hydroxyl adenines and guanines, 5-trifluoro-methyl uracils and cytosines, and 7-methylguanine or inosine.

The protecting group may be attached to $B_1$ and $B_2$. Examples of the protecting group may include, but are not limited to, benzoyl or isobutyryl, acetyl, dimethylformiainidine (DMF), phenoxyacetyl (PAC) and its derivative, and 4-t-butylphenoxyacetyl (TAC).

The reaction conditions for coupling of the compound of Formula 1 to the compound of Formula 2 are the same as those for coupling of the nucleotide dimer or trimer as described hereinbefore.

Further, the present invention provides a method for preparing a nucleotide dimer [(rNMP)$_2$], comprising coupling a compound of Formula 3 and a compound of Formula 2:

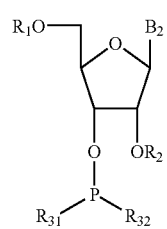

(3)

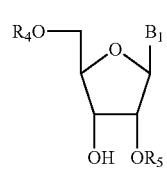

(2)

In Formulae 2 and 3, $R_1$, $R_2$, $R_4$ and $R_5$ are each independently hydrogen (—H) or protecting groups, and $B_1$ and $B_2$ are each independently nucleosidic bases.

Preferably, examples of the protecting groups $R_1$ and $R_4$ may independently include, but are not limited to, hydrogen (—H), dimethoxytrityl, monomethoxytrityl, trityl, and 9-phenyl xanthen-9-yl (pixyl). Examples of suitable groups for $R_2$ and $R_5$ may include, but are not limited to, t-butyl-dimethylsilyl, tri-isopropyl silyloxymethyl (TOM), 1-(2-chloro ethoxy)ethyl (CEE), 2-cyanoethoxymethyl (CEM), bis(2-acetoxy)methyl (ACE), 1-(2-fluorophenyl)-4-methoxypiperidin-4-yl (Fpmp), 1-(4-chloro phenyl)-4-ethoxypiperidin-4-yl (Cpep), 1-[2-chloro-4-methyl)phenyl]-4-methoxy piperidin-4-yl (Ctmp), 4-nitrophenylethylsulfonyl (NPES), 4-chloro phenylethylsulfonyl (CPES), 1-(2-cyanoethoxy) ethyl (CNEE), trimethyl silylethoxymethyl (SEM), methoxyethoxymethyl (MEM), levulinyl, 4-nitropheylethyl (NPE), and 4-nitrophenylethyloxycarbonyl (NPEOC). Examples of suitable groups for $R_{31}$ may include, but are not limited to, cyanoalkyloxy (such as cyanoethoxy and cyanomethoxy), 4-cyano-2-butenyloxy, and diphenylmethylsilylethoxy. Non-limiting examples of suitable groups for $R_{32}$ may include dialkylamino. $B_1$ and $B_2$ are each independently adenine, cytosine, guanine, uracil or derivatives thereof.

More preferably, in Formula 3, $R_1$ is hydrogen (—H) or dimethoxytrityl, $R_2$ is tert-butyl-dimethylsilyl, $R_{31}$ is 2-cyanoethoxy, and $R_{32}$ is dialkylamino (most preferably diisopropylamino).

The coupling of the compound of Formula 4 to the compound of Formula 3 in the present invention may be carried out in the same manner as above, and a more preferred activator is 5-ethylthiotetrazole.

In addition, the present invention provides a ribonucleotide trimer represented by Formula 6:

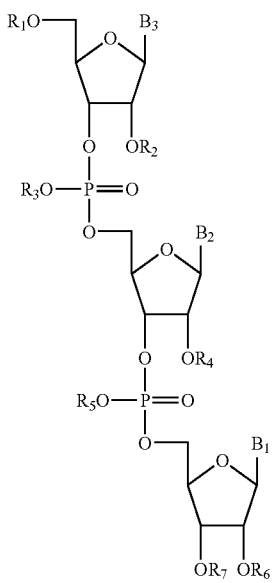

(6)

wherein $R_1$, $R_2$, $R_3$, $R_4$, $R_5$ and $R_6$ are each independently hydrogen (—H) or protecting groups, $B_1$, $B_2$ and $B_3$ are each independently nucleosidic bases, and $R_7$ is hydrogen or

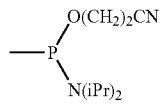

wherein iPr is isopropyl.

Preferred is the ribonucleotide trimer of Formula 6 wherein $R_1$ is hydrogen (—H) or dimethoxytrityl; $R_2$, $R_4$ and $R_6$ are each t-butyl-dimethylsilyl; and $R_3$ and $R_5$ are halogen-substituted phenyl.

Further, the present invention provides a method for preparing a nucleotide timer, comprising the steps of
(a) reacting a ribonucleotide dimer of Formula 4 with an acid to remove $R_1$ of Formula 4; and
(b) coupling the resulting product of Step (a) to a ribonucleoside T-phosphoramidite to prepare a ribonucleotide trimer.

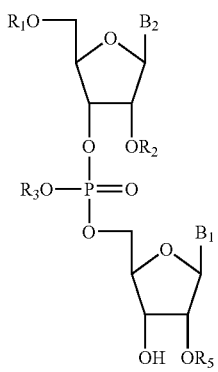

(4)

In Formula 4, $R_1$, $R_2$, $R_3$ and $R_5$ are each independently protecting groups, and $B_1$ and $B_2$ are each independently nucleosidic bases.

In Formula 4, preferred examples of the protecting group $R_1$ may include, but are not limited to, dimethoxytrityl, monomethoxytrityl, trityl, and pixyl (9-phenyl xanthen-9-yl). Examples of suitable groups for $R_2$ and $R_5$ may include, but are not limited to, t-butyl-dimethylsilyl, tri-isopropyl silyloxymethyl (TOM), 1-(2-chloro ethoxy)ethyl (CEE), 2-cyanoethoxymethyl (CEM), bis(2-acetoxy)methyl (ACE), 1-(2-fluorophenyl)-4-methoxypiperidin-4-yl (Fpmp), 1-(4-chloro phenyl)-4-ethoxypiperidin-4-yl (Cpep), 1-[2-chloro-4-methyl)phenyl]-4-methoxy piperidin-4-yl (Ctmp), 4-nitrophenylethylsulfonyl (NPES), 4-chloro phenylethylsulfonyl (CPES), 1-(2-cyanoethoxy)ethyl (CNEE), trimethyl silylethoxymethyl (SEM), methoxyethoxymethyl (MEM), levulinyl, 4-nitropheylethyl (NPE), and 4-nitrophenylethyloxycarbonyl (NPEOC). Examples of suitable groups for $R_3$ may include, but are not limited to hydrogen, and halogen-substituted phenyl or carbobenzoxyl. $B_1$ and $B_2$ are each independently adenine, cytosine, guanine, uracil or derivatives thereof.

More preferably, in Formula 4, $R_1$ is dimethoxytrityl, $R_2$ is tert-butyl-dimethylsilyl, $R_3$ is hydrogen or halogen-substituted phenyl (most preferably chlorophenyl), and $R_5$ is tert-butyl-dimethylsilyl.

Removal of $R_1$ from the ribonucleotide dimer of Formula 4 may be carried out by any conventional deprotection method known in the art, using a strong acid, for example, benzenesulfonic acid. For example, a hydrogen (—H) may be positioned in $R_1$ by reacting the ribonucleotide dimer of Formula 4 with the strong acid.

The coupling conditions of Step (b) in the above preparation method are the same as those conditions mentioned as above.

Advantageous Effects

The present invention enables the efficient high-speed and high-purity synthesis of nucleotide oligomers. The method of the present invention provides a nucleotide oligomer having 15-20% higher purity than the conventional art.

Mode for Invention

Now, the present invention will be described in more detail with reference to the following Examples. These examples are provided only for illustrating the present invention and should not be construed as limiting the scope and spirit of the present invention.

Hereinafter, the measured $^{31}$P-NMR values are values as measured using Varian Mercury Plus 300 MHz.

EXAMPLE I

Synthesis of Ribonucleotide Dimers (Phosphotriester Method)

[Reaction Scheme 1]

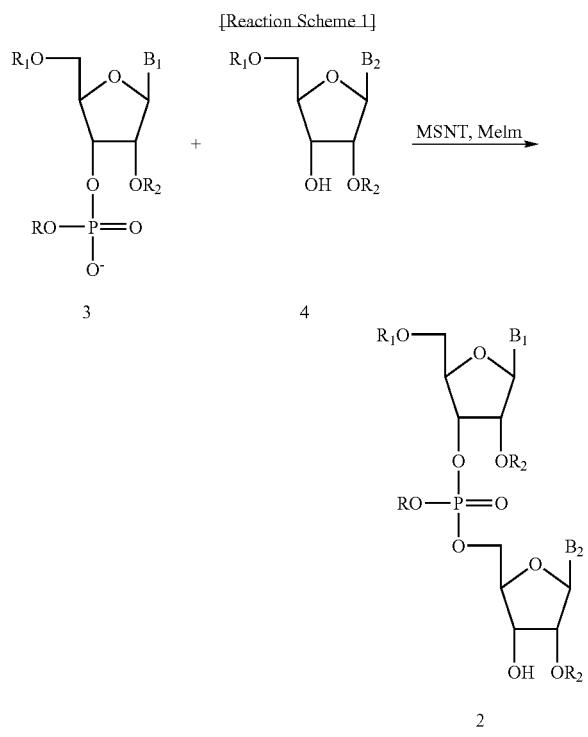

Synthesis of ribonucleotide dimers UpU, CpU and GpA (2b to 2d)

$R_1$=DMTr (dimethoxytrityl), $R_2$=TBDMS (tert-butyldimethylsilyl), R=o-chlorophenyl. 2a-$B_1$=U, $B_2$=U; 2b-$B_1$=bzC, $B_2$=U; 2c-$B_1$=ibG, $B_2$=bzA; 3a-$B_1$=U; 3-b $B_1$=bzC; 3c-$B_1$=ibG; 4a-$B_2$=U; 4b-$B_2$=bzA. bz=benzoyl, ib=isobutyryl

EXAMPLE 1

Synthesis of 5'-O-dimethoxytrityl-2'-O-t-butyldimethylsilyluridine-3'-O-(2-chlorophenylphosphate)-5'-O-2'-O-(t-butyldimethylsilyl)uridine (2a)

Step 1: Synthesis of 5'-O-dimethoxytrityl-2-O-t-butyldimethylsilyluridine-3'-042-chlorophenylphosphate) (triethylammonium salt) (3a)

Triazole (0.63 g, 9.24 mmol, Sigma Aldrich) and anhydrous triethylamine (1.3 mL, 9.15 mmol, Sigma Aldrich) were dissolved in dioxane (20 mL), and the solution was cooled to 5° C., A solution of O-chlorophenyl phosphodichloridate (1.1 g, 4.53 mmol, Sigma Aldrich) in 5 mL of dioxane was added dropwise to the resulting solution. After one hour, the mixed solution was filtered and added to 5'-O-dimethoxytrityl-2'-O-t-butyldimethylsilyluridine (4a, 2 g, 3.02 mmol) in 10 mL of pyridine which had been cooled to −5° C. Then, 1-methylimidazole (0.38 mL, 4.6 mmol, Sigma Aldrich) was added thereto. After one hour, 0.1 M triethylammonium bicarbonate buffer (TEAB, 10 mL) was added to the above cooled solution which was then concentrated. The residue was dissolved in dichloromethane (50 mL) and washed with 0.1 M TEAB (50 mL), and the aqueous layer was extracted two times with 20 mL of dichloromethane. The organic layer was collected, washed with 0.1 M TEAB (100 mL), and dried over sodium sulfate. The residue was concentrated using a vacuum pump to give 2.78 g (yield: 97%) of the title compound.

Step 2: Synthesis of 5'-O-dimethoxytrityl-2'-O-(t-butyldimethylsilyOuridine-3'-O-chlorophenylphosphate-5'-O-2'-O-(t-butyldimethylsilyburidine (2a)

5'-O-dimethoxytrityl-2'-O-tert-butyldimethylsilyluridine-3 chlorophenylphosphate)triethylammonium salt (3a, 1.47 g, 1.54 mmol) prepared in Step 1 and 2'-O-tert-butyldimethylsilyluridine generated from the treatment of 5'-O-dimethoxytrityl-2'-O-tert-butyldimethylsilyluridine (4a, 0.5 g, 1.4 mmol) with dichloroacetic acid (DCA) were dissolved in 20 mL of pyridine and the solution was dried using a vacuum pump. 1-mesitylenesulfonyl-3-nitro-1,2,4-triazole (MSNT, 0.68 g, 2.31 mmol, Sigma Aldrich) in 5 mL of fresh pyridine was added to the dried product. The reaction solution was concentrated to about 3 mL, and 0.16 mL of 1-methylimidazole (1.89 mmol) was added thereto. After one hour, the reaction solution was cooled to 0° C. and 2 mL of water was then added thereto. The reaction solution was concentrated. The residue oil was dissolved in 15 mL of dichloromethane and washed with 15 mL of 0.1 M TEAB. The aqueous layer was washed with dichloromethane (3×5 mL). The organic layer was collected and dried over sodium sulfate. The residue was purified by silica gel chromatography to afford the title compound (0.68 g, yield: 41%).

$^{31}$P NMR (DMSO), $\delta_{ppm}$: −6.38, −6.25

EXAMPLE 2

Synthesis of 5'-O-dimethoxytrityl-$N^4$-benzoyl-2'-O-(t-butyldimethylsilyl)cytidine-3'-O-(2-chlorophenylphosphate)-5'-O-2'-O-(t-butyldimethylsilyburidine (2b)

Step 1: Synthesis of 5'-O-dimethoxytrityl-$N^4$-benzoyl-2'-O-(t-butyldimethylsilyl)cytidine-3'-O-(2-chlorophenylphosphate)(triethylammonium salt) (3b)

Triazole (0.69 g, 10 mmol) and anhydrous triethylamine (1.4 mL, 9.9 mmol) were dissolved in dioxane (20 mL) and the solution was cooled to 5° C. A solution of O-chlorophenyl phosphodichloridate (1.2 g, 4.90 mmol) in 5 mL of dioxane was added dropwise to the resulting solution. After one hour, the mixed solution was filtered and added to 5'-O-dimethoxytrityl-$N^4$-benzoyl-2'-O-(t-butyldimethylsilyl)cytidine (2.5 g, 3.27 mmol, Sigma Aldrich) in 10 mL of anhydrous pyridine which had been cooled to −5° C. Then, 1-methylimidazole (0.40 mL, 4.9 mmol, Sigma Aldrich) was added to the above solution. After one hour, 0.1 M TEAB (10 mL) was added to the cooled solution that was then concentrated. The residue was dissolved in dichloromethane (50 mL) and washed with 0.1 M TEAB (50 mL). The aqueous layer was extracted two times with 20 mL of dichloromethane. The organic layer was collected, washed with 0.1 M TEAB (100 mL), dried over sodium sulfate and concentrated using a vacuum pump to give 3.08 g (yield: 94%) of the title compound.

Step 2: Synthesis of 5'-O-dimethoxytrityl-N⁴-benzoyl-2'-O-(t-butyldimethylsilyl)cytidine-3'-O-(2-chlorophenylphosphate-5'-O-2'-O-(t-butyldimethylsilyburidine (2b)

5'-O-dimethoxytrityl-N⁴-benzoyl-2'-O-t-butyldimethyl silyl)cytidine-3'-O-(2-chlorophenylphosphate)(triethylammonium salt) (3b, 3.24 g, 3.07 mmol) prepared in Step 1 and 2'-O-tert-butyldimethylsilyluridine generated from the treatment of 5'-O-dimethoxytrityl-2"-O-tert-butyldimethylsilyluridine (4a, 1 g, 2.8 mmol) with dichloroacetic acid (DCA) ( ) were dissolved in 20 mL of pyridine, and the solution was dried using a vacuum pump. MSNT (1.364 g, 4.61 mmol) in 10 mL of fresh pyridine was added to the dried product. The reaction solution was concentrated to about 3 mL and 0.25 mL of 1-methylimidazole (3.07 mmol) was added thereto. After one hour, the reaction solution was cooled to 0° C. and 2 mL of water was added thereto. After the reaction solution was concentrated, the residue oil was dissolved in 15 mL of dichloromethane and washed with 15 mL of 0.1 M TEAB. The aqueous layer was washed with dichloromethane (3×5 mL), and the organic layer was collected and dried over sodium sulfate. The residue was purified by silica gel chromatography to afford the title compound (1.47 g, yield: 40%).

$^{31}$P NMR (DMSO), $\delta_{ppm}$: −6.42, −6.10

EXAMPLE 3

Synthesis of 5'-O-dimethoxytrityl-N²-isobutyryl-2'-O-(t-butyldimethylsilyl)guanosine-3'-O-chlorophenylphosphate-5'-O-2'-O-(t-butyldimethylsilyl)adenine (2c)

Step 1: Synthesis of 5'-O-dimethoxytrityl-N²-isobutyryl-2-O-(t-butyldimethylsilyl)guanosine-3'-O-(2-chlorophenylphosphate)(triethylammonium salt) (3c)

Triazole (1.37 g, 19.87 mmol) and anhydrous triethylamine (2.8 mL, 19.87 mmol) were dissolved in dioxane (20 mL) and the solution was cooled to 5° C. A solution of O-chlorophenyl phosphodichloridate (2.386 g, 9.74 mmol) in 5 mL of dioxane was added dropwise to the resulting solution. After one hour, the mixed solution was filtered and added to 5'-O-dimethoxytrityl-N²-isobutyryl-2'-O-t-butyldimethylsilylguanosine (5 g, 6.5 mmol) in 10 mL of anhydrous pyridine which had been cooled to −5° C. Then, 1-methylimidazole (0.80 mL, 9.74 mmol) was added thereto. After one hour, 0.1 M TEAB (10 mL) was added to the cooled solution which was then concentrated. The residue was dissolved in dichloromethane (50 mL) and washed with 0.1 M TEAB (50 mL), and the aqueous layer was extracted with dichloromethane (2×20 mL). The organic layer was collected, washed with 0.1 M TEAB (100 mL), dried over sodium sulfate and concentrated using a vacuum pump to give 6.55 g (yield: 95%) of the title compound.

Step 2: Synthesis of 5'-O-dimethoxytrityl-N²-isobutyryl-2'-O-(t-butyldimethylsilyl) guanosine-3'-O-(2-chlorophenylphosphate)-5'-O-2'-O-(t-butyldimethylsilyl)adenine (2c)

5'-O-dimethoxytrityl-N²-isobutyryl-2'-O-(t-butyldimethylsilyl)guano sine-3'-O-(2-chlorophenylphosphate)(triethylammonium salt) (3c, 1.34 g, 1.26 (nmol) prepared in Step 1 and N⁴-Benzoyl-2'-O-tert-butyldimethylsilyladenine generated from the treatment of 5'-O-dimethoxytrityl-N⁴-Benzoyl-2'-O-tert-butyldimethylsilyladenine (4b, 1 g, 2.8 mmol) with dichloroacetic acid (DCA) were dissolved in 20 mL of pyridine, and the solution was dried using a vacuum pump. MSNT (0.6 g, 1.89 mmol) dissolved in 10 mL of fresh pyridine was added to the dried product. The reaction solution was concentrated to about 3 mL and 0.16 mL of 1-methylimidazole (1.89 mmol) was added thereto. After 30 min, the reaction solution was cooled to 0° C. and 2 mL of water was then added to the solution. The reaction solution was concentrated, and the residue oil was dissolved in 15 mL of dichloromethane and washed with 15 mL of 0.1 M TEAB. The aqueous layer was washed with dichloromethane (3×5 mL), and the organic layer was collected and dried over sodium sulfate. The residue was purified by silica gel chromatography to afford the title compound (1.265 g, yield: 84%).

$^{31}$P NMR (DMSO), $\delta_{ppm}$: −6.33, −6.14

EXAMPLE II

Synthesis of Ribonucleotide Dimer (Phosphoramidite Method)

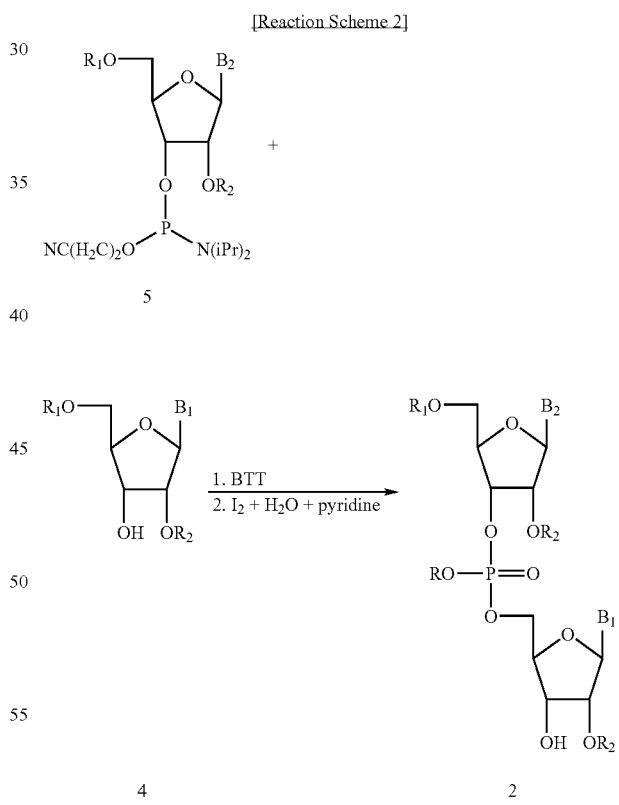

[Reaction Scheme 2]

Synthesis of ribonucleotide dimers UU, CU, GU and GA (1a to 1d).

$R_1$=DMTr, $R_2$=TBDMS, R=2-cyanoethyl. 1a-$B_1$=U, $B_2$=U, 1b-$B_1$=bzC, $B_2$=U, 1c-$B_1$=ibG, $B_2$=U, 1d-$B_1$=ibGU, $B_2$=bzA, 2d-$B_1$=U, $B_2$=U, 2e $B_1$=bzC, $B_2$=U, 2f-$B_1$=ibG, $B_2$=U, 2 g-$B_1$=ibG, $B_2$=bzA. 4a-$B_2$=U, 4b-$B_2$=bzA. 5a-$B_1$=U, 5b -$B_1$=bzC, 5c-$B_1$=ibG.

EXAMPLE 4

Synthesis of 5'-O-dimethoxytrityl-P-cyanoethylphosphoryl-2'-O-(t-butyldimethylsilyl)uridyl-3'-O-[(N,N-diisopropylamino)cyanoethoxyphosphino](3'->5')-2'-O-t-butyldimethylsilyluridine (2d)

5'-dimethoxytrityl-uridine-2'-O-t-butyldimethylsilyl-3'-[(2-cyanoethyl)-(N,N-diisopropyl)]phosphoramidite (5a, 1.085 g, 1.26 mmol) and 2'-O-t-butyldimethylsilyluridine generated from the treatment of 5'-O-dimethoxytrityl-2'-O-t-butyldimethylsilyluridine (4a, 0.3 g, 0.84 mmol) with dichloroacetic acid (DCA), were dissolved in 10 mL of anhydrous acetonitrile, and the solution was concentrated until it became gum. 5-benzylthiotetrazole (0.483 g, 2.52 mmol, ChemGene) was dissolved in 20 mL of acetonitrile, and the solution was concentrated until crystals were formed. Two solutions were combined using 20 mL of acetonitrile and concentrated to 3 mL. After one hour, the combined solution was cooled to 0° C., and a 0.5 M iodine solution in 7.6 mL of THF:pyridine:water (7:1:2) was added thereto. The resulting solution was allowed to stand at room temperature for 5 min, and 3.8 mL of a 2 M $Na_2S_2O_3$ aqueous solution was then added thereto. After the solution was concentrated until it became gum, the residue was dissolved in 20 mL of dichloromethane and the aqueous layer was extracted with dichloromethane (3×5 mL). The organic layer was collected, washed with a 0.1 M TEAB aqueous solution (3×10 mL), and dried over sodium sulfate. The solution was concentrated and evaporated with toluene (2×10 mL) to remove the remaining pyridine. The residue was dissolved in dichloromethane and was purified by silica gel chromatography to afford the title compound (0.5 g, yield: 53%).

$^{31}$P NMR (DMSO), $\delta_{ppm}$: −1.03, −0.71

EXAMPLE 5

Synthesis of 5'-O-dimethoxytrityl-$N^4$-benzoyl-P-cyanoethylphosphoryl-2'-O-(t-butyldimethylsilyl)cytidyl-3'-O-[(N,N-diisopropylamino)cyanoethoxyphosphino] (3'->5')-2'-O-t-butyldimethylsilyluridine (2e)

5'-dimethoxytrityl-$N^4$-benzoylcytidine-2'-O-t-butyldimethylsilyl-3'-[(2- cyano ethyl)-(N,N-diisopropyl)]phosphoramidite (5b, 1.928 g, 2.00 mmol) and 2'-O-t-butyldimethylsilyluridine generated from the treatment of 5'-O-dimethoxytrityl-2'-O-t-butyldimethylsilyluridine (4a, 0.358 g, 1.00 mmol) with dichloroacetic acid (DCA) (were dissolved in 10 mL of anhydrous acetonitrile, and the solution was concentrated until it became gum. 5-ethylthiotetrazole (0.528 g, 4 mmol, Sigma Aldrich) was dissolved in 20 mL of acetonitrile, and the solution was concentrated until crystals were formed. Two solutions were combined using 20 mL of acetonitrile. Thereafter, the combined solution was concentrated to 3 mL and cooled to 0° C. after 4 hours, and a 0.5 M iodine solution in 12 mL of THF:pyridine:water (7:1:2) was then added thereto. This solution was allowed to stand at room temperature for 5 min and 6 mL of a 2 M $Na_2S_2O_3$ aqueous solution was added thereto. The solution was concentrated until it became gum. The residue was then dissolved in 20 mL of dichloromethane and the aqueous layer was extracted with dichloromethane (3×5 mL). The organic layer was collected, washed with a 0.1 M TEAB aqueous solution (3×10 mL), and dried over sodium sulfate. The solution was concentrated and evaporated with toluene (2×10 mL) to remove the remaining pyridine. The residue was dissolved in dichloromethane and purified by silica gel chromatography to afford the title compound (0.868 g, yield: 70%).

$^{31}$P NMR (DMSO), $\delta_{ppm}$: −1.05, −0.74

EXAMPLE 6

Synthesis of 5'-O-dimethoxytrityl-$N^2$-isobutyryl-P-cyanoethylphosphoryl-2'-O-(t-butyldimethylsilyl)guanosyl-3'-O-[(N,N-diisopropylamino)cyanoethoxyphosphino](3'->5'-2'-O-t-butyldimethylsilyluridine 5'-dimethoxytrityl-$N^2$-isobutyrylguanosine-2'-O-t-butyldimethylsilyl-3'-[(2-cyanoethyl)-(N,N-diisopropyl)]phosphoramidite (5c, 3.48 g, 3.59 mmol) and 2'-O-t -butyldimethylsilyluridine generated from the treatment of 5'-O-dimethoxytrityl-2'-O-t-butyldimethylsilyluridine (4a, 0.644 g, 1.8 mmol) with dichloroacetic acid (DCA) were dissolved in 10 mL of anhydrous acetonitrile, and the solution was concentrated until it became gum. 5-benzylthiotetrazole (0.379 g, 7.18 mmol) was dissolved in 20 mL of acetonitrile and the solution was concentrated until crystals were formed. Two solutions were combined using 20 mL of acetonitrile. Thereafter, the combined solution was concentrated to 3 mL and cooled to 0° C. after 1.5 hours, and a 0.5 M iodine solution in 22 mL of THF:pyridine:water (7:1:2) was then added thereto. This solution was allowed to stand at room temperature for 5 min and 11 mL of a 2 M $Na_2S_2O_3$ aqueous solution was added thereto. After the solution was concentrated until it became gum, the residue was dissolved in 20 mL of dichloromethane and the aqueous layer was extracted with dichloromethane (3×5 mL). The organic layer was collected, washed with a 0.1 M TEAB aqueous solution (3×10 mL), and dried over sodium sulfate. The solution was concentrated and evaporated with toluene (2×10 mL) to remove the remaining pyridine. The residue was dissolved in dichloromethane and purified by silica gel chromatography to afford the title compound (1.126 g, yield: 50%).

$^{31}$P NMR (DMSO), $\delta_{ppm}$: −0.52, −0.68

EXAMPLE 7

Synthesis of 5'-O-dimethoxytrityl-$N^2$-isobutyryl-P-cyanoethylphosphoryl-2'-O-(t-butyldimethylsilyl)guanosyl-3'-O-[(N,N-diisopropylamino)cyanoethoxyphosphino] (3'->5')-$N^4$-benzoyl-2'-O-t-butyldimethylsilyladenine (2 g)

5'-dimethoxytrityl-$N^2$-isobutyrylguanosine-2'-O-t-butyldimethylsilyl-3'-[(2-cyanoethyl)-(N,N-diisopropyl)]phosphoramidite (5c, 2.8 g, 2.88 mmol) and $N^4$-benzoyl-2'-O-t-butyldimethylsilyladenine generated from the treatment of 5'-O-dimethoxytrityl-$N^4$-benzoyl-2'-O-t-butyldimethylsilyladenine (4b, 0.7 g, 1.44 mmol) with dichloroacetic acid (DCA) were dissolved in 10 mL of anhydrous acetonitrile, and the solution was concentrated until it became gum. 5-benzylthiotetrazole (1.075 g, 5.6 mmol) was dissolved in 20 mL of acetonitrile and the solution was concentrated until crystals were formed. Thereafter, two solutions were combined using 20 mL of acetonitrile. The combined solution was concentrated to 3 mL and cooled to 0° C. after 1.5 hours, and a 0.5 M iodine solution in 18 mL of THF:pyridine:water (7:1:2) was then added thereto. This solution was allowed to stand at room temperature for 5 min and 9 mL of a 2 M $Na_2S_2O_3$ aqueous solution was added thereto. The solution was concentrated until it became gum. The residue was dissolved in 20 mL of dichloromethane and the aqueous layer was extracted with dichloromethane (3×5 mL). The organic layer was collected, washed with a 0.1 M TEAB aqueous solution (3×10 mL), and dried over sodium sulfate. The solution was concentrated and evaporated with toluene (2×10 mL) to remove the remaining pyridine. The residue was dissolved in dichloromethane and purified by silica gel chromatography to afford the title compound (2.182 g, yield: 96%). $^{31}$P NMR (DMSO), $\delta_{ppm}$: −0.69, −0.81

EXAMPLE III

Synthesis of RNA dimer phosphoramidites

[Reaction Scheme 3]

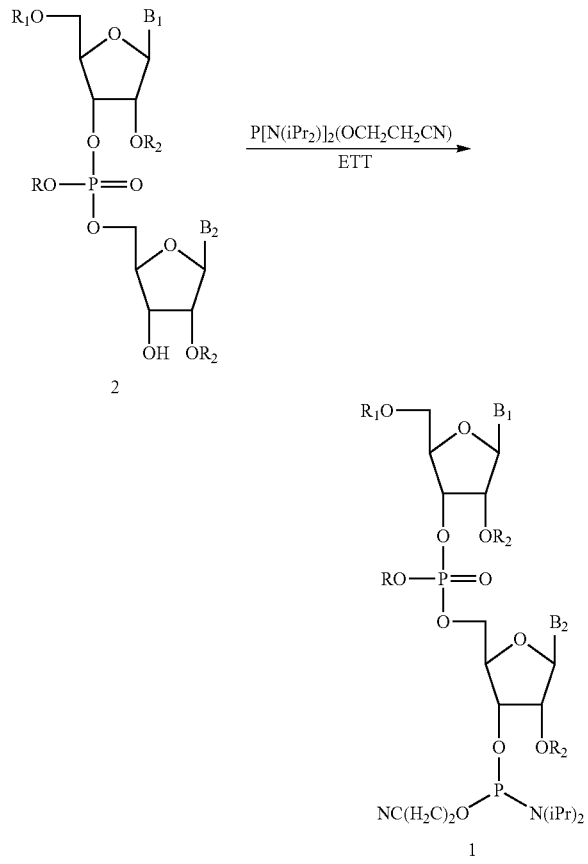

Synthesis of RNA ribonucleotide dimer phosphoramidites UU, CU, GU and GA (1a to 1d)

$R_1$=DMTr, $R_2$=TBDMS, R=2-cyanoethyl. 1a-$B_1$=U, $B_2$=U, 1b-$B_1$=bzC, $B_2$=U, 1c-B=ibG, $B_2$=U, 1d-$B_1$=ibGU, $B_2$=bzA, 2d-$B_1$=U, $B_2$=U, 2e-$B_1$ bzC, $B_2$=U, 2f-$B_1$=ibG, $B_2$=U, 2 g-$B_1$=ibG, $B_2$=bzA. 4a-$B_2$=U, 4b-$B_2$=bzA. 5a-$B_1$=U, 5b -$B_1$=bzC, 5c-$B_1$=ibG.

EXAMPLE 8

Synthesis of 5'-O-dimethoxytrityl-P-cyanoethylphosphoryl-2'-O-(t-butyldimethylsilyl)uridyl-3'-O-[(N,N-diisopropylamino)cyanoethoxyphosphino] (3'->5')-2'-O-t-butyldimethylsilyluridine (1a)

Compound 2d of Example 4 (0.503 g, 0.44 mmol) and 5-ethylthiotetrazole (0.074 g, 0.57 mmol) were dissolved in 10 mL of acetonitrile and the solution was concentrated. 10 mL of acetonitrile was placed in a reaction flask which was then filled with argon, and bis-(diisopropylamino)-2-cyanoethoxy phosphine (0.17 mL, 0.57 mmol) was added dropwise thereto. The reaction solution was concentrated to about 1 mL, allowed to stand for 2 hours and then completely concentrated. The residue was dissolved in 10 mL of dichloromethane and saturated with a saturated NaHCO$_3$ aqueous solution. The organic layer was washed with a saturated NaHCO$_3$ aqueous solution (5×20 mL) and dried over sodium sulfate. The reaction solution was completely concentrated and water was added until the solution became turbid. Purification was carried out using a LiChroprep RP18 resin (Merck & Co., Inc., USA) to give the title compound (0.4 g, yield: 70%).

$^{31}$P NMR (DMSO), $\delta_{ppm}$: ~138.4, ~148.9, ~−1.03, ~−0.73

EXAMPLE 9

Synthesis of 5'-O-dimethoxytrityl-N$^4$-benzoyl-P-cyanoethylphosphoryl-2'-O-(t-butyldimethylsilyl)cytidyl-3'-O-[(N,N -diisopropylamino)cyanoethoxyphosphino] (3'->5')-2'-O-t-butyldimethylsilyluridine (1b)

Compound 2e of Example 5 (0.868 g, 0.70 mmol) and 5-ethylthiotetrazole (0.11 g, 0.84 mmol) were dissolved in 10 mL of acetonitrile and the solution was concentrated. 10 mL of acetonitrile was placed in a reaction flask which was then filled with argon, and bis-(diisopropylamino)-2-cyanoethoxy phosphine (0.17 mL, 0.57 mmol) was added dropwise thereto. The reaction solution was concentrated to about 1 mL, allowed to stand for 4 hours and then completely concentrated. The residue was dissolved in 10 mL of dichloromethane and saturated with a saturated NaHCO$_3$ aqueous solution. The organic layer was washed with a saturated NaHCO$_3$ aqueous solution (5×20 mL) and dried over sodium sulfate. The reaction solution was completely concentrated and water was added until the solution became turbid. Purification was carried out using a LiChroprep RP18 resin to give the title compound (0.58 g, yield: 60%).

$^{31}$P NMR (DMSO), $\delta_{ppm}$: ~148.7, ~143.9, ~−1.18, ~−0.77

EXAMPLE 10

Synthesis of 5'-O-dimethoxytrityl-N$^2$-isobutyryl-P-cyanoethylphosphoryl-2'-O-(t-butyldimethylsilyl)guanosyl-3'-O-[(N,N-diisopropylamino)cyanoethoxyphosphino] (3'->5')-2'-O-t-butyldimethylsilyluridine (1e)

Compound 2f of Example 6 (1.126 g, 0.09 mmol) and 5-ethylthiotetrazole (0.15 g, 1.17 mmol) were dissolved in 10 mL of acetonitrile and the solution was concentrated. 10 mL of acetonitrile was placed in a reaction flask which was then filled with argon, and bis-(diisopropylamino)-2-cyanoethoxy phosphine (0.35 mL, 1.17 mmol) was added dropwise thereto. The reaction solution was concentrated to about 1 mL, allowed to stand for 4 hours and then completely concentrated. The residue was dissolved in 10 mL of dichloromethane and saturated with a saturated NaHCO$_3$ aqueous solution. The organic layer was washed with a saturated NaHCO$_3$ aqueous solution (5×20 mL) and dried over sodium sulfate. The reaction solution was completely concentrated and water was added until the solution became turbid. Purification was carried out using a LiChroprep RP18 resin to give the title compound (0.75 g, yield: 57%).

$^{31}$P NMR (DMSO), $\delta_{ppm}$: ~150, ~148.9, ~−0.66, ~−0.49

EXAMPLE 11

Synthesis of 5'-O-dimethoxytrityl-$N^2$-isobutyryl-P-cyanoethylphosphoryl-2'-O-(t-butyldimethylsilyl) guanosyl-3'-O-[(N,N-diisopropylamino)cyanoethoxyphosphino] (3->5')-$N^4$-benzoyl-2'-O-t-butyldimethylsilyladenine (1d)

Compound 2 g of Example 7 (1.5 g, 1.09 mmol) and 5-ethylthiotetrazole (0.18 g, 1.42 mmol) were dissolved in 10 mL of acetonitrile and the solution was concentrated. 10 mL of acetonitrile was placed in a reaction flask which was then filled with argon, and bis-(diisopropylamino)-2-cyanoethoxy phosphine (0.43 mL, 1.42 mmol) was added dropwise thereto. The reaction solution was concentrated to about 1 mL, allowed to stand for 4 hours and then completely concentrated. The residue was dissolved in 10 mL of dichloromethane and saturated with a saturated $NaHCO_3$ aqueous solution. The organic layer was washed with a saturated $NaHCO_3$ aqueous solution (5×20 mL) and dried over sodium sulfate. The reaction solution was completely concentrated and water was added until the solution became turbid. Purification was carried out using a LiChroprep RP18 resin to give the title compound (1.081 g, yield: 63%).

$^{31}$P NMR (DMSO), $\delta_{ppm}$: ~150, ~148.8, ~−0.63, ~−0.41

EXAMPLE IV

Synthesis of RNA Trinucleotides

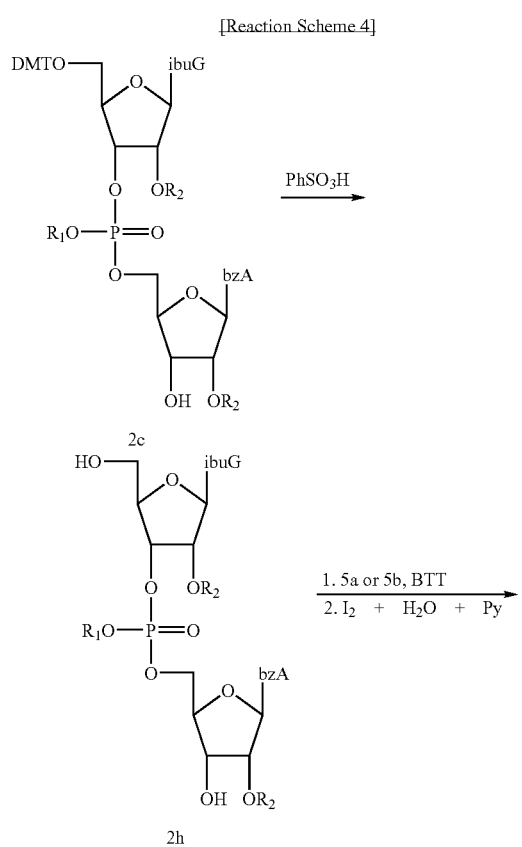

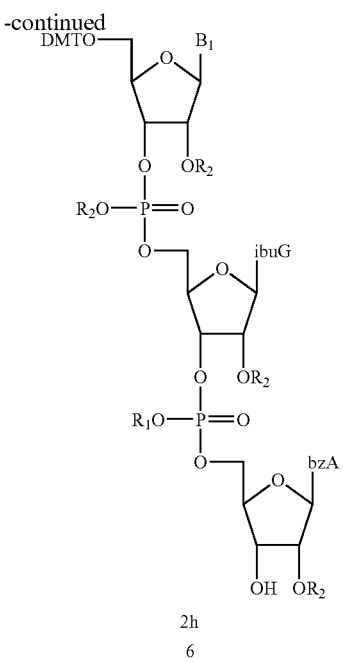

Synthesis of RNA trinucleotides UGpA (6a) and CGpA (6b)

$R_1$=o-chlorophenyl, $R_2$=TBDMS. 6a-$B_1$=U, 6b-$B_1$=bzC

EXAMPLE 12

Synthesis of 5'-O-dimethoxytrityl-$N^2$-isobutyryl-2'-O-(t-butyldimethylsilyl)uridin-3'-yl chlorophenylphosphat-5'-yl $N^2$-isobutyrylguanosin-3'-yl $N^4$-benzoyl-2'-13-t-butyldimethylsilyladenin-5'-yl cyanoethylphosphate (6a)

Step 1: Synthesis of $N^2$-isobutyryl-2'-O-(t-butyldimethylsilyl)guanosine-3'-yl chlorophenyl phosphate-5'-yl $N^4$-benzoyl-2'-O-t-butyldimethylsilyladenine (2 h)

9 mL of 4% benzenesulfonic acid was added to a dichloromethane:methanol (7:3) solution which was then cooled to 0° C. The solution was added to Compound 2c (1.265 g, 0.88 mmol) dissolved in 9 mL of a dichloromethane:methanol (7:3) solution and allowed to stand at 0° C. for 3 min. 25 mL of a saturated $NaHCO_3$ aqueous solution was added thereto, and the organic layer was washed with a saturated $NaHCO_3$ aqueous solution, dried over sodium sulfate and concentrated. The residue was purified by silica gel chromatography to afford the title compound (0.62 g, yield: 63%).

Step 2: Synthesis is of 5'-O-dimethoxytrityl-$N^2$-isobutyryl-2'-O-(t-butyldimethylsilyl)uridin-3'-yl chlorophenylphosphat-5'-yl $N^2$-isobutyrylguanosin-3'-yl $N^4$-benzoyl-2'-O-t-buryldimethylsilyladenin-5'-yl cyanoethylphosphate (6a)

U phosphoramidite (5a, 0.335 g, 0.39 mmol) and the compound of Step 1 (2 h, 0.292 g, 0.26 mmol) were dissolved in anhydrous acetonitrile and the solution was concentrated. A reaction flask was filled with argon gas and 10 mL of anhydrous acetonitrile was added thereto. 5-benzylthiotetrazole (0.15 g, 0.78 mmol) was dissolved in 10 mL of anhydrous acetonitrile and the solution was concentrated until crystals were formed, and then added to the nucleoside solution. The reaction solution was concentrated to about 3 mL and allowed to stand for 2 hours. The reaction solution was cooled to 0° C., and a 0.5M iodine solution in 2.4 mL of THF:pyridine:water (7:1:2) was added thereto. The resulting solution was allowed to stand at room temperature for 5 min, and 1.2 mL of a 2 M Na$_2$S$_2$O$_3$ aqueous solution was then added to the solution. After the solution was concentrated until it became gum, the residue was dissolved in 20 mL of dichloromethane, and the organic layer was washed with a 0.1 M TEAB aqueous solution. The aqueous layer was extracted with dichloromethane (3×5 mL). The organic layer was collected, washed with a 0.1 M TEAB aqueous solution (3×10 mL), and dried over sodium sulfate. The solution was concentrated and evaporated with toluene (2×10 mL) to remove the remaining pyridine. The residue was dissolved in dichloromethane and purified by silica gel chromatography to afford the title compound (0.413 g, yield: 84%).

$^{31}$P NMR (DMSO), $\delta_{ppm}$: −6.3, −1.4

EXAMPLE 13

Synthesis of 5'-O-dimethoxytrityl-N$^4$-benzoyl-2'-O-(t-butyldimethylsilyl)cytidin-3'-yl chlorophenylphosphat-5'-yl N$^4$-isobutyrylguanosin-3-yl N$^4$-benzoyl-2'-O-t-butyldimethylsilyladenin-5'-yl cyanoethylphosphate (6b)

rC phosphoramidite (5b, 0.409 g, 0.42 mmol) and the compound of Step 1 of Example 12 (2 h, 0.238 g, 0.21 mmol) were dissolved in anhydrous acetonitrile and concentrated. A reaction flask was filled with argon gas and 10 mL of anhydrous acetonitrile was added thereto. 5-benzylthiotetrazole (0.123 g, 0.64 mmol) was dissolved in 10 mL of anhydrous acetonitrile and the solution was concentrated until crystals were formed, and then added to the nucleoside solution. The reaction solution was concentrated to about 3 mL and allowed to stand for 3 hours. The reaction solution was cooled to 0° C., and a 0.5M iodine solution in 2.6 mL of THF:pyridine:water (7:1:2) was added thereto. The resulting solution was allowed to stand at room temperature for 5 min, and 1.3 mL of a 2 M Na$_2$S$_2$O$_3$ aqueous solution was then added thereto. After the solution was concentrated until it became gum, the residue was dissolved in 20 mL of dichloromethane, and the organic layer was washed with a 0.1 M TEAB aqueous solution. The aqueous layer was extracted with dichloromethane (3×5 mL). The organic layer was collected, washed with a 0.1 M TEAB aqueous solution (3×10 mL), and dried over sodium sulfate. The solution was concentrated and evaporated with toluene (2×10 mL) to remove the remaining pyridine. The residue was dissolved in dichloromethane and purified by silica gel chromatography to afford the title compound (0.298 g, yield: 71%).

$^{31}$P NMR (DMSO), $\delta_{ppm}$: −6.3, −1.2

EXAMPLE V

Synthesis of Ribonucleotide Trimer Phosphoramidites

[Reaction Scheme 5]

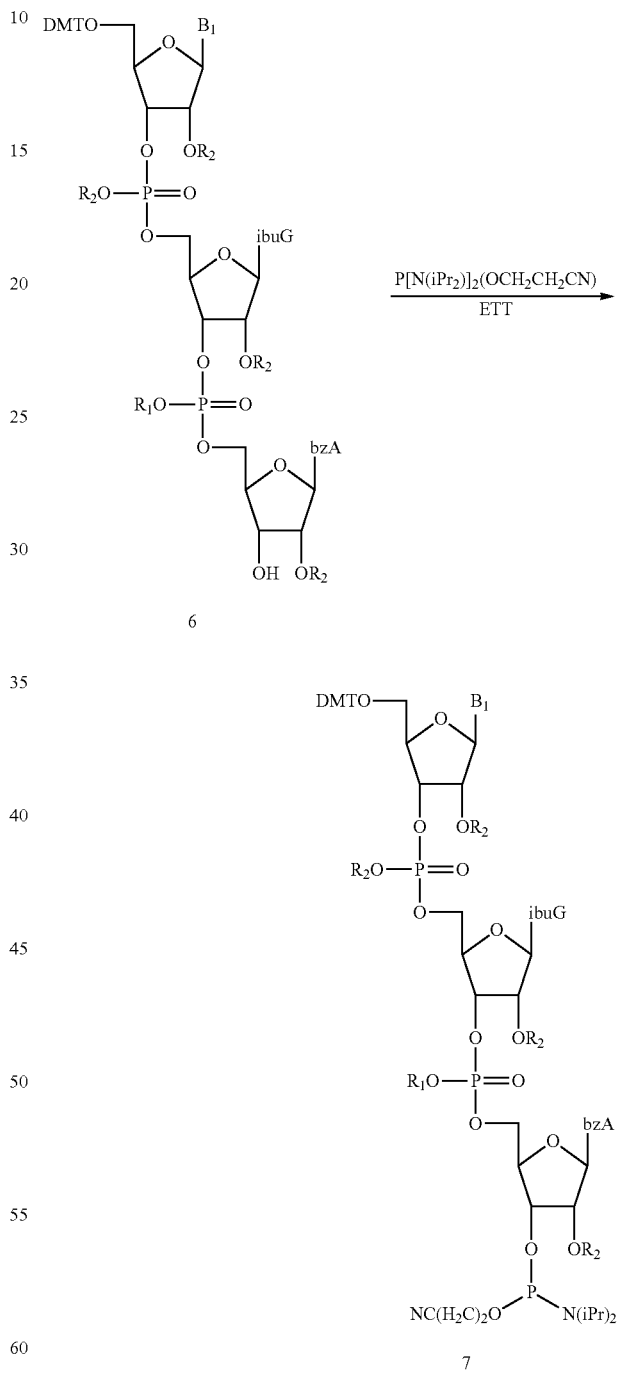

Synthesis of ribonucleotide trimer phosphoramidites (7a and 7b)

R$_1$=o-chlorophenyl, R$_2$=2-cyanoethyl, R$_3$=TBDMS. 6a, 7a-B$_1$=U, 6b, 7b B$_1$=bzC

EXAMPLE 14

Synthesis of 5'-O-dimethoxytrityl-2'-O-(t-butyldimethylsilyl)uridin-3'-yl chlorophenylphosphat-5'-yl N²-isobutyrlguanosine-3'-yl N⁴-benzoyl-2'-O-t-butyldimethylsilyladenin-5'-yl cyanoethylphosphate-3-O-(2-cyanoethyl)-N,N-diisopropylphosphoramidite (7a)

Compound 6a of Example 12 (0.41 g, 0.21 mmol) and 5-ethylthiotetrazole (0.037 g, 0.57 mmol) were dissolved in 10 mL of anhydrous acetonitrile and concentrated. 10 mL of anhydrous acetonitrile was placed in a reaction flask which was then filled with argon, and bis-(diisopropylamino)-2-cyanoethoxy phosphine (0.084 mL, 0.28 mmol) was added dropwise thereto. The reaction solution was concentrated to about 1 mL and allowed to stand for 4 hours, followed by complete concentration. The residue was dissolved in 10 mL of dichloromethane and saturated with a saturated NaHCO₃ aqueous solution. The organic layer was washed with a saturated NaHCO₃ aqueous solution (5×20 mL) and dried over sodium sulfate. The reaction solution was completely concentrated and water was added until the solution became turbid. Purification was carried out using a LiChroprep RP18 resin to give the title compound (0.319 g, yield: 72%).
³¹P NMR (DMSO), $\delta_{ppm}$: ~150.2, ~148.9, ~−6, ~−1.4

EXAMPLE 15

Synthesis of 5'O-dimethoxytrityl-N⁴-benzoyl 2'-O-(t-butyldimethylsilyl)cytidin-3'-yl chlorophenylphosphat-5' yl N⁴-isobutyrylguanosin-3'-yl N⁴-benzoyl-2'-O-t-butyldimethylsilyladenin-5'-yl cyanoethylphosphate-3-O-(2-cyanoethyl)-N,N-diisopropylphosphoramidite (7b)

Compound 6b of Example 13 (0.298 g, 0.15 mmol) and 5-ethylthiotetrazole (0.025 g, 0.20 mmol) were dissolved in 10 mL of anhydrous acetonitrile and concentrated. 10 mL of anhydrous acetonitrile was placed in a reaction flask which was then filled with argon, and bis-(diisopropylamino)-2-cyanoethoxy phosphine (0.06 mL, 0.20 mmol) was added dropwise thereto. The reaction solution was concentrated to about 1 mL and allowed to stand for 4 hours, followed by complete concentration. The residue was dissolved in 10 mL of dichloromethane and saturated with a saturated NaHCO₃ aqueous solution. The organic layer was washed with a saturated NaHCO₃ aqueous solution (5×20 mL) and dried over sodium sulfate. The reaction solution was completely concentrated and water was added until the solution became turbid. Purification was carried out using a LiChroprep RP18 resin to give the title compound (0.180 g, yield: 60%).
³¹P NMR (DMSO), $\delta_{ppm}$: ~150.2, ~148.9, ~−6, ~−1.0

EXAMPLE VI

Synthesis of siRNAs using RNA dimer phosphoramidites

All of siRNAs were synthesized using a Polygen DNA/RNA synthesizer (Polygen) on a 0.8 µmol scale in a trityl-off mode. The 3'-tenninus employed RNA CPG. The RNA CPG (Glen Research) was used in an amount of 30 µmol/g loading, and monomer bases were respectively $rA^{tac}$, $rC^{tac}$, $rG^{tac}$ and U phosphoramidites (Proligo). The monomer and dimer phosphoramidites were each used in the form of a 0.05 M solution thereof in acetonitrile. Equivalents of the monomers and dimers were each 2.5 equivalents per cycle. An activator was 0.5 M 5-ethylthiotetrazole (in acetonitrile). Solid supports and protecting groups were deprotected by heating the reaction solution at 65° C. for 2 hours using a mixture of aqueous ammonia and ethanol (3:1), and the solution was freeze-dried. The residue was dissolved in 0.4 mL of an N-methylpyridone:triethylamine:triethylamine trihydrofluoride (6:3:4) solution and heated at 65° C. for 2 hours. 4 mL of n-butyl alcohol was added to the resulting solution which was then cooled in a refrigerator for 2 hours and centrifuged to obtain solid siRNAs, followed by freeze-drying. The yield of crude siRNAs was quantitatively analyzed using a UV spectrophotometer at 260 nm and the purity thereof was analyzed by reverse-phase HPLC. Extinction coefficients of naturally-occurring ribonucleotides for concentration calculation are as follows: rA, 15400: rC, 7200: U, 9900: and rG, 11500. A molecular weight of each siRNA was confirmed by mass analysis using MALDI-TOF (Broker, Autoflex).

EXAMPLE 16

Synthesis of GFP-Sense siRNA Using GU RNA Dimer

GFP-sense siRNA had a sequence of 5'-GUU CAG CGU GUC CGG CGA GUU-3' (SEQ ID NO: 1). Synthesis of siRNA was carried out analogously to Example 15, and a coupling period of time for dimer GU and monomers was each 10 min. The dimer used for the first coupling step was GU, to which monomer units were then attached. Purity of the product was measured by reverse-phase chromatography, and an analyzer was an Agilent 1100 system. Chromatography buffer was a mixture of 100 mM TEAA (pH 7.0) and acetonitrile. Purity and yield of the siRNA product were compared with those of the GFP-sense siRNA which was obtained using the monomer instead of the dimer as the first ribonucleotide, The results are given in Table 1 below.

TABLE 1

| First ribonucleotide | Purity of siRNA |
| --- | --- |
| Monomer | 52% |
| Dimer | 73% |

EXAMPLE 17

Synthesis of GFP-Antisense siRNA Using CU RNA Dimer

GFP-antisense siRNA had a sequence of 5'-CUC GCC GGA CAC GCU GAA CUU-3' (SEQ ID NO: 2). Synthesis of siRNA was carried out analogously to Example 15, and a coupling period of time for dimer CU and monomers was each 10 min. The dimer used for the first coupling step was CU, to which monomer units were then attached. Purity of the product was measured by reverse-phase chromatography, and an analyzer was an Agilent 1100 system. Chromatography buffer was a mixture of 100 mM TEAA (pH 7.0) and acetonitrile. Purity and yield of the siRNA product were compared with those of the GFP-antisense siRNA which was obtained using the monomer instead of the dimer as the first ribonucleotide. The results are given in Table 2 below.

TABLE 2

| First ribonucleotide | Purity of siRNA |
|---|---|
| Monomer | 63% |
| Dimer | 78% |

EXAMPLE 18

Synthesis of JNK-Antisense siRNA Using UU RNA Dimer

JNK-antisense siRNA had a sequence of 5'-AGA AGG UAG GAC AUU CUU UUU-3'(SEQ ID NO: 3). Synthesis of siRNA was carried out analogously to Example 15, and a coupling period of time for dimer UU and monomers was each 10 min. The dimer used for the first coupling step was UU, to which monomer units were then attached. Purity of the product was measured by reverse-phase chromatography, and an analyzer was an Agilent 1100 system. Chromatography buffer was a mixture of 100 mM TEAA (pH 7.0) and acetonitrile. Purity and yield of the siRNA product were compared with those of the INK-antisense siRNA which was obtained using the monomer instead of the dimer as the first ribonucleotide. The results are given in Table 3 below.

TABLE 3

| First ribonucleotide | Purity of siRNA |
|---|---|
| Monomer | 71% |
| Dimer | 88% |

EXAMPLE 19

Synthesis of SEI-Sense siRNA Using GA RNA Dimer

SEI-sense siRNA had a sequence of 5'-GCA AGG GUC UGA AGC GGAA-3' (SEQ ID NO: 4). Synthesis of siRNA was carried out analogously to Example 15, and a coupling period of time was 10 min and 15 min for monomers and dimer GA, respectively. The dimer used for the first coupling step was GA, to which monomer units were then attached. Purity of the product was measured by reverse-phase chromatography, and an analyzer was an Agilent 1100 system. Chromatography buffer was a mixture of 100 mM TEAA (pH 7.0) and acetonitrile. Purity and yield of the siRNA product were compared with those of the SEI-sense siRNA which was obtained using the monomer instead of the dimer as the first ribonucleotide. The results are given in Table 4 below.

TABLE 4

| First ribonucleotide | Purity of siRNA |
|---|---|
| Monomer | 65% |
| Dimer | 78% |

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The present invention enables the efficient high-speed and high-purity synthesis of nucleotide oligomers. The method of the present invention provides a nucleotide oligomer having 15-20% higher purity than the conventional art.

What is claimed is:

1. A method for preparing ribonucleotide oligomers having a desired sequence, comprising:
   (A) extending a ribonucleotide chain consisting essentially of (a) coupling a ribonucleotide dimer to a ribonucleoside attached to solid supports or to universal solid supports as a starting material; and (b) sequentially coupling ribonucleotide monomers to the resulting structures of Step (a) to prepare ribonucleotide oligomers; and
   (B) removing the ribonucleotide oligomers from the solid supports.

2. The method of claim 1, wherein the ribonucleotide monomer is a ribonucleoside phosphoramidite.

3. The method of claim 1, wherein the ribonucleotide oligomer is one containing at least one ribonucleotide selected from 2'-halogen ribonucleotide, 2'-amino ribonucleotide, 2'-O-alkyl ribonucleotide and 2'-O-alkoxyalkyl ribonucleotide.

4. The method of claim 1, wherein the ribonucleotide oligomer has a phosphodiester, phosphoramidate, alkylphosphoramidate, alkylphosphonate, phosphorothioate, alkylphosphotriester, or alkylphosphonothioate linkage.

5. The method of claim 4, wherein the ribonucleotide oligomer has a phosphodiester or phosphoramidate linkage.

6. The method of claim 1, wherein the ribonucleotide includes a sugar in which a methyl or an ethyl is bonded to —OH of a C2 carbon.

7. The method of claim 1, wherein the ribonucleotide includes a sugar in which a fluoro (—F) or an amino is bonded to a C2 carbon instead of —OH.

8. The method of claim 3, wherein the 2'-halogen ribonucleotide includes 2'-fluoro-ribonucleotide.

9. The method of claim 3, wherein the 2'-O-alkyl ribonucleotide includes 2'-O-methyl ribonucleotide.

10. The method of claim 3, wherein the 2'-O-alkoxyalkyl ribonucleotide includes 2'-O-methoxyethyl-ribonucleotide.

11. A method for preparing ribonucleotide oligomers having a desired sequence, comprising:
   (A) extending a ribonucleotide chain, consisting of (a) coupling a ribonucleotide dimer to a ribonucleoside attached to solid supports or to universal solid supports as a starting material; and (b) sequentially coupling ribonucleotide monomers to the resulting structures of Step (a) to prepare ribonucleotide oligomers; and
   (B) removing the ribonucleotide oligomers from the solid supports.

* * * * *

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: GFP-sense siRNA

<400> SEQUENCE: 1
guucagcgug uccggcgagu u                                        21

<210> SEQ ID NO 2
<211> LENGTH: 21
<212> TYPE: RNA
<213> ORGANISM: Artificial Sequence
<220> FEATURE:
<223> OTHER INFORMATION: GFP-antisense siRNA

<400> SEQUENCE: 2
cucgccggac acgcugaacu u                                        21

<210> SEQ ID NO 3
<211> LENGTH: 21
<212> TYPE: RNA
<213> ORGANISM: Artificial Sequence
<220> FEATURE:
<223> OTHER INFORMATION: JNK-antisense siRNA
```

```
<400> SEQUENCE: 3
agaagguagg acauucuuuu u                                        21

<210> SEQ ID NO 4
<211> LENGTH: 19
<212> TYPE: RNA
<213> ORGANISM: Artificial Sequence
<220> FEATURE:
<223> OTHER INFORMATION: SEI-sense siRNA

<400> SEQUENCE: 4
gcaagggucu gaagcggaa                                           19
```